(12) United States Patent
Zhu

(10) Patent No.: US 8,050,773 B2
(45) Date of Patent: Nov. 1, 2011

(54) EXPANDABLE NEUROMODULAR STIMULATION LEAD

(76) Inventor: Jie Zhu, Ambler, PA (US)

( * ) Notice: Subject to any disclaimer, the term of this patent is extended or adjusted under 35 U.S.C. 154(b) by 507 days.

(21) Appl. No.: 12/239,795

(22) Filed: Sep. 28, 2008

(65) Prior Publication Data

US 2010/0082086 A1    Apr. 1, 2010

(51) Int. Cl.
*A61N 1/05*    (2006.01)
(52) U.S. Cl. .......................... 607/117; 607/126; 607/130
(58) Field of Classification Search .................. None
See application file for complete search history.

(56) References Cited

U.S. PATENT DOCUMENTS

| | | | |
|---|---|---|---|
| 3,348,548 A | 10/1967 | Chardack | |
| 4,285,347 A | 8/1981 | Hess | |
| 4,519,403 A | 5/1985 | Dickhudt | |
| 5,344,439 A | 9/1994 | Otten | |
| 5,545,206 A * | 8/1996 | Carson | 607/126 |
| 5,702,438 A | 12/1997 | Avitall | |
| 5,733,322 A | 3/1998 | Starkebaum | |
| 6,066,165 A | 5/2000 | Racz | |
| 6,161,047 A | 12/2000 | King et al. | |
| 6,353,762 B1 | 3/2002 | Baudino et al. | |
| 6,564,078 B1 | 5/2003 | Marino et al. | |
| 6,638,276 B2 | 10/2003 | Sharkey et al. | |
| 6,658,302 B1 | 12/2003 | Kuzma et al. | |
| 6,697,676 B2 | 2/2004 | Dahl et al. | |
| 6,741,878 B2 * | 5/2004 | Fuimaono et al. | 600/374 |
| 6,745,079 B2 * | 6/2004 | King | 607/117 |
| 7,047,086 B2 * | 5/2006 | Taskiran et al. | 607/126 |
| 7,177,702 B2 | 2/2007 | Wallace et al. | |
| 7,231,260 B2 | 6/2007 | Wallace et al. | |
| 7,363,089 B2 | 4/2008 | Vinup et al. | |
| 2005/0096718 A1 | 5/2005 | Gerber et al. | |
| 2006/0041295 A1 | 2/2006 | Osypka | |

(Continued)

FOREIGN PATENT DOCUMENTS

WO    W09304734    3/1993

OTHER PUBLICATIONS

Zhu, J, F Falco, CO Onyewu, Y Joesphson, R Vesga, and R Jari. "Alternative approach to needle placement in spinal cord stimulator trial/implantation." Pain Physician, Jan./Feb. 2011: 14(1):45-53.

(Continued)

*Primary Examiner* — Carl H Layno
*Assistant Examiner* — Paula J Stice
(74) *Attorney, Agent, or Firm* — Dovas Law, P.C.

(57) ABSTRACT

A medical stimulation lead is provided. The medical stimulation lead includes an elongated lead body including a substantially rounded cross-section and including a first biased portion forming a first section of the substantially rounded cross-section and a second biased portion forming a second section of the substantially rounded cross-section. A plurality of electrodes are provided connected to the elongated lead body. A restraining body is removably connected to the elongated lead body releasably exerting a force substantially counter to the biases of the first biased portion and the second biased portion. The retraining body releasably maintains the substantially rounded cross-section of the elongated lead body, wherein removal of the restraining body permits the first biased portion and the second biased portion to expand, dividing the substantially rounded cross-section. The present invention further provides a method for providing spinal cord stimulation and a stimulation lead including an elongated plate.

22 Claims, 11 Drawing Sheets

U.S. PATENT DOCUMENTS

| | | |
|---|---|---|
| 2007/0055332 A1 | 3/2007 | Swoyer |
| 2007/0255373 A1 | 11/2007 | Metzler et al. |
| 2008/0103504 A1 | 5/2008 | Schmitz et al. |

OTHER PUBLICATIONS

Zhu, J, et al. "Alternative approach to needle placement in cervical spinal cord stimulator insertion." Pain Physician, Mar./Apr. 2011: 14(2):195-210.

Math Open definition; plane; www.mathopenref.com/plane.html; Aceessed May 4, 2011.

Definition of plane from Oxford Dictionaries Online; http://oxforddictionaries.com/view/entry/m_en_us1278560?rskey=J8x; copyright 2011 Oxford University Press.

Definition of rounded from Oxford Dictionaries Online; http://oxforddictionaries.com/view/entry/m_en_us1285970#m_en_usl; copyright 2011 Oxford University Press.

Definition of rounded from Macmillan Dictionary; www.macmillandictionary.com/dictionary/american/rounded; Macmillan Publishers Limited 2009-2011.

Oscar Vega; Math 260 Perspectives in Geometry; definition of a circle; Spring 2011.

Math Open definition; circle; www.mathopenref.com/circle.html; Accessed May 5, 2011.

About.com, Inc. Leads and Electrodes on Neurostimulators Routing the New Signals that will Mask Your Pain. Dec. 11, 2009. http://backandneck.about.com/od/painmanagement/ig/SCS/Leads-and-Electrodes.htm (accessed Jun. 3, 2011).

Arachnoiditis Sufferers Action and Monitoring Society (ASAMS) New Zealand Inc. Anatomy of the Epidural Space. Jul. 25, 2003. http://www.arachnoiditis.info/content/articles/epidural_space_anatomy/Epidural%20Space%20Anatomy.htm (accessed May 18, 2011).

Medtronic Inc. What is Neurostimulation? http://www.medtronic.com/IN/physicians/pain/neurostimulation.html (accessed Jun. 3, 2011).

Orthopaedic Spine Center, LLC. A Patients Guide To: Spinal Cord Stimulation. Aug. 20, 2007. http://www.orthopaedicandspinecenter.com/office/office/spinal-cord-stimulato-pt-leaflet.pdf (accessed Jun. 3, 2011).

Smith, CC, JL Lin, M Shoka, SS Dosanjh, and D MD Casthely. "A Report of Paraparesis Following Spinal Cord Stimulator Trial, Implantation and Revision." Pain Physician, Jul./Aug. 2010: 13:357-363.

St. Jude Medical, Inc. "Percutaneous & Paddle Lead Families" Sep. 2010.

Zhang, Y, MJ Wood, and C Gilligan. "Spinal Cord Stimulation in a Patient with Spinal Epidural Lipomatosis." Pain Medicine, Feb. 2011.

\* cited by examiner

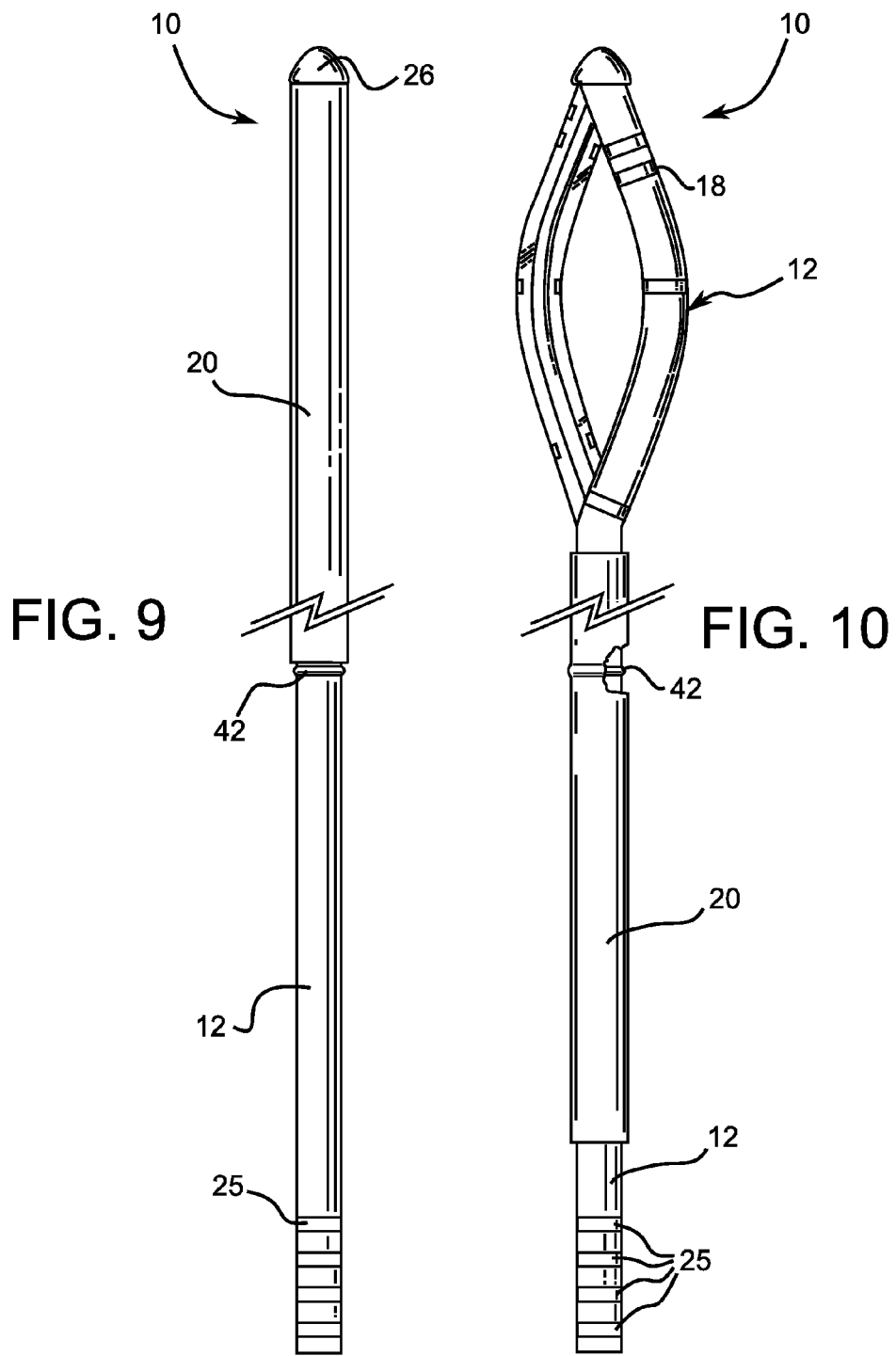

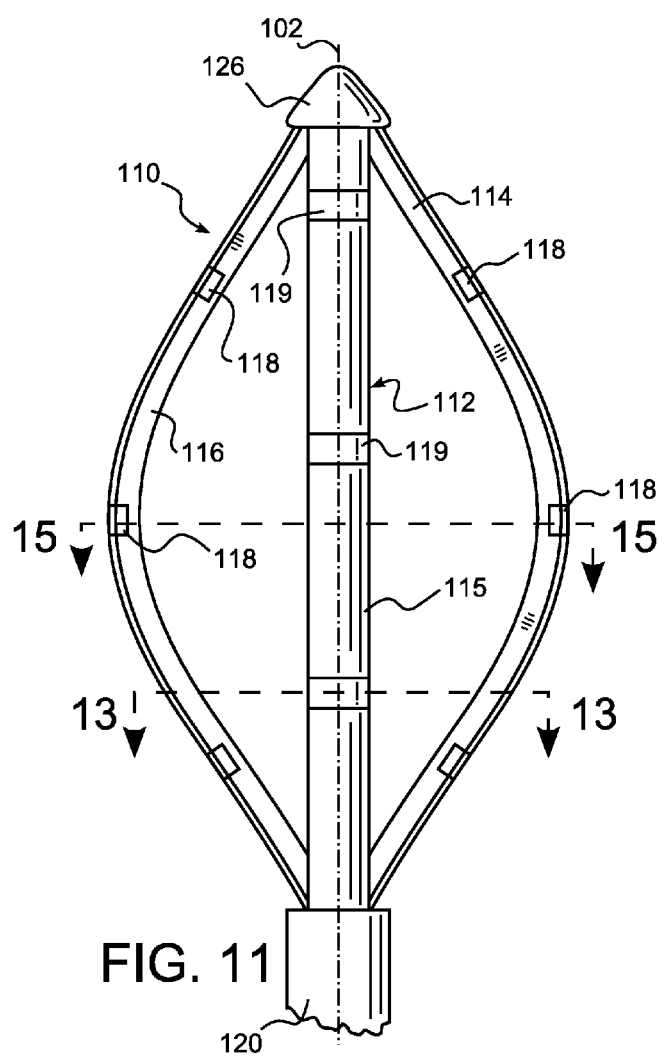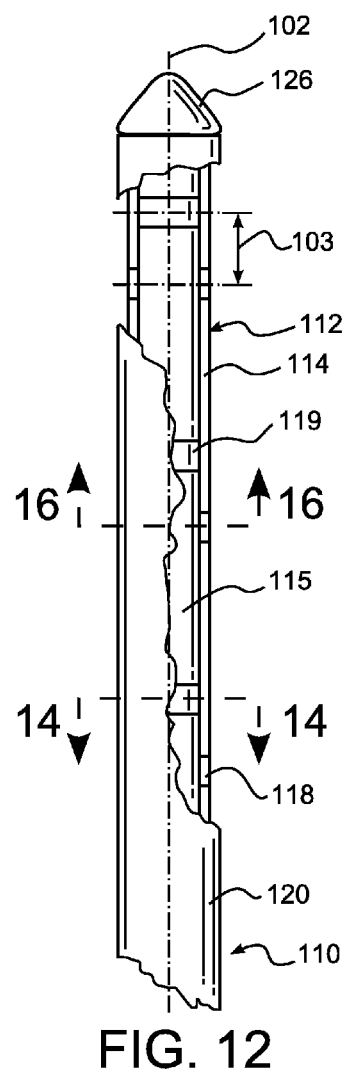
FIG. 11
FIG. 12

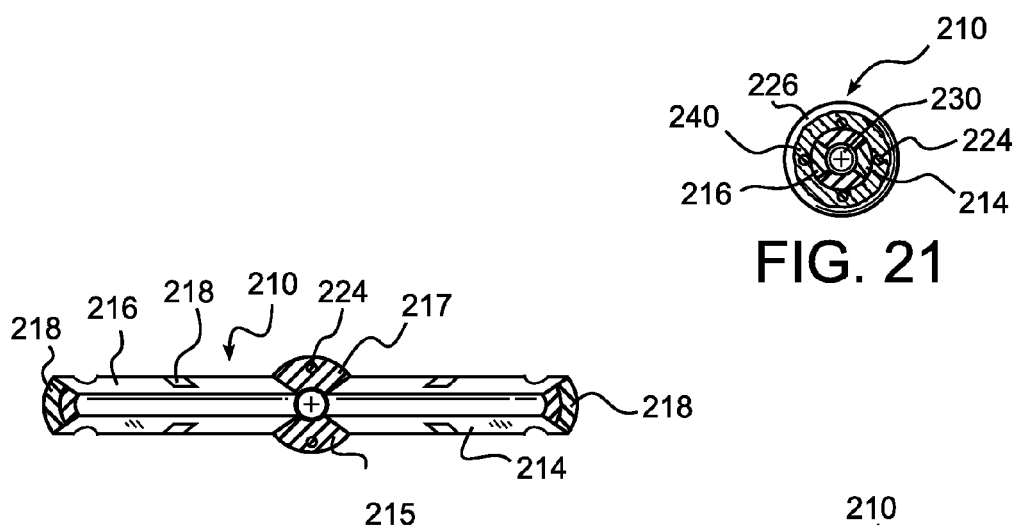
FIG. 21
FIG. 20
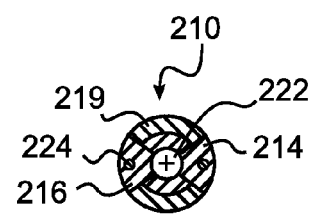
FIG. 19

EXPANDABLE NEUROMODULAR STIMULATION LEAD

BACKGROUND

Neuromodular stimulation, including spinal cord stimulation, peripheral nerve stimulation and deep brain stimulation, has been used for the treatment of various ailments including chronic pain. Spinal cord stimulation in particular, has for some time been used to treat cervical radicular pain from the neck to the arms and lumbar radicular pain from the lower back to the legs. During a treatment implementing spinal cord neuromodular stimulation, a lead including current-carrying electrodes is inserted into a patient's spinal canal posterior to the spinal cord, and electric potential is applied to the electrodes to provide electrical stimulation to overpower and obscure pain signals transmitted from an affected area of the body to the spine. This electrical stimulation typically causes the patient to feel a tingling sensation instead of the pain attributable to the patient's particular ailment.

There are two types of leads commonly used for neuromodular stimulation, a percutaneous lead which can be relatively easily inserted through an epidural needle into the spinal canal, and a paddle lead which must be placed in the spinal canal via an invasive surgical procedure. Percutaneous leads include a wire-like elongated body, which while relatively easily inserted, are often instable in the spinal canal and not easily accurately and precisely positioned. Also, percutaneous leads have a relatively narrow stimulation area and do not allow for lateral displacement of electrodes, and therefore, stimulating current typically may only travel longitudinally along the lead, potentially limiting a treatment's therapeutic effects. Two percutaneous leads may be inserted parallel side by side in the spinal canal to provide a wide stimulation area allowing stimulating current to travel between the two leads. However, positioning two percutaneous leads parallel in such a manner is difficult and time consuming. Conversely, paddle leads are typically constructed of a flattened body which may be accurately and precisely positioned in a relatively stable manner. The form of a typical paddle lead allows for a wide stimulation area with lateral displacement of electrodes permitting lateral current flow perpendicular to a longitudinal axis of the paddle lead. However, the invasive procedure required for placing paddle leads may result in significant patient discomfort and extended recovery time. Also, once placed, paddle leads may not be easily removed or adjusted to accommodate patient preference or treatment requirements.

Modified percutaneous leads have been proposed to provide for greater stability during lead placement. However, such modified forms typically suffer from deficiencies in ease of placement, precision and accuracy of placement, safety, usability, and effectiveness.

It would be desirable to provide a medical stimulation lead which may be easily, safely, accurately, precisely, and stably placed within a spinal canal. Once placed in a spinal canal, such medical stimulation lead should be easily removed and adjusted as required to accommodate patient preference or treatment requirements. Such lead should further accommodate a wide stimulation area and lateral displacement of electrodes.

SUMMARY

The present invention provides a medical stimulation lead including an elongated lead body including a substantially rounded cross-section and including a first biased portion forming a first section of the substantially rounded cross-section and a second biased portion forming a second section of the substantially rounded cross-section. A plurality of electrodes are provided connected to the elongated lead body for conducting current. A restraining body is removably connected to the elongated lead body releasably exerting a force substantially counter to the biases of the first biased portion and the second biased portion. The retraining body releasably maintains the substantially rounded cross-section of the elongated lead body, and removal of the restraining body permits the first biased portion and the second biased portion to expand, dividing the substantially rounded cross-section.

The present invention further provides a method for providing spinal cord stimulation. The method includes providing a medical stimulation lead including an elongated lead body including a substantially rounded cross-section and a longitudinal axis, wherein the elongated lead body includes a biased portion biased in a direction substantially away from the longitudinal axis. The method further includes providing the medical stimulation lead with a plurality of electrodes connected to the elongated lead body, and providing a restraining body removably connected to the biased portion. A force counter to the bias of the biased portion is exerted with the restraining body to maintain the substantially rounded cross-section of the elongated lead body. The medical stimulation lead is inserted into an epidural space in a body of a user. The restraining body is removed from the biased portion to release the force counter to the bias to expand the biased portion away from the longitudinal axis, dividing the substantially rounded cross-section and stabilizing the medical stimulation lead in the epidural space. An electric potential between two or more of the plurality of electrodes is provided.

The present invention further provides a medical stimulation lead including an elongated lead body including an elastically deformable elongated plate. The elongated plate includes a first surface and a second surface which in an undeformed state is angled with respect to the first surface along an axis running longitudinally along the length of the elongated lead body. The first surface includes a first edge, the second surface includes a second edge, and the first edge forms an acute angle with the second edge. The elongated plate is releasably rollable into a substantially cylindrical form. A plurality of electrodes for conducting current are connected to the elongated plate. An outer cannula is slideably connected to the elongated lead body and removably surrounds the elongated plate releasably exerting a force on the elongated plate to releasably maintain the substantially cylindrical form of the elongated plate. An end of the outer cannula is in removable and slideable contact with the first edge and the second edge of the elongated plate.

BRIEF DESCRIPTION OF THE DRAWING(S)

The foregoing Summary as well as the following detailed description will be readily understood in conjunction with the appended drawings which illustrate preferred embodiments of the invention. In the drawings:

FIG. 9 is an elevation view showing a full length of the medical stimulation lead of FIG. 1.

FIG. 10 is an elevation view showing a full length of the medical stimulation lead of FIG. 1 in an expanded position.

FIG. 11 is a front elevation view of a medical stimulation lead in an expanded position according to a second preferred embodiment of the present invention.

FIG. 12 is a front elevation view of the medical stimulation lead of FIG. 9 shown in a contracted position.

FIG. 19 is a cross-section view of the medical stimulation lead of FIG. 18 taken along line 19-19 of FIG. 18.

FIG. 20 is a cross-section view of the medical stimulation lead of FIG. 17 taken along line 20-20 of FIG. 17.

FIG. 21 is a cross-section view of the medical stimulation lead of FIG. 18 taken along line 21-21 of FIG. 18.

DETAILED DESCRIPTION OF THE PREFERRED EMBODIMENT(S)

Figure 1:
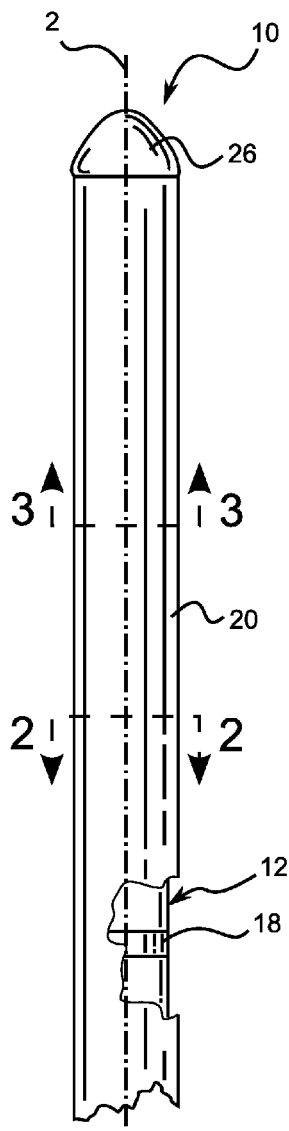
FIG. 1 is an elevation view of a medical stimulation lead in a contracted position according to a first preferred embodiment of the present invention.

Certain terminology is used in the following description for convenience only and is not limiting. The words "right," "left," "top," and "bottom" designate directions in the drawings to which reference is made. The words "a" and "one" are defined as including one or more of the referenced item unless specifically stated otherwise. This terminology includes the words above specifically mentioned, derivatives thereof, and words of similar import. The phrase "at least one" followed by a list of two or more items, such as A, B, or C, means any individual one of A, B or C as well as any combination thereof.

The preferred embodiments of the present invention are described below with reference to the drawing figures where like numerals represent like elements throughout.

Figure 4:
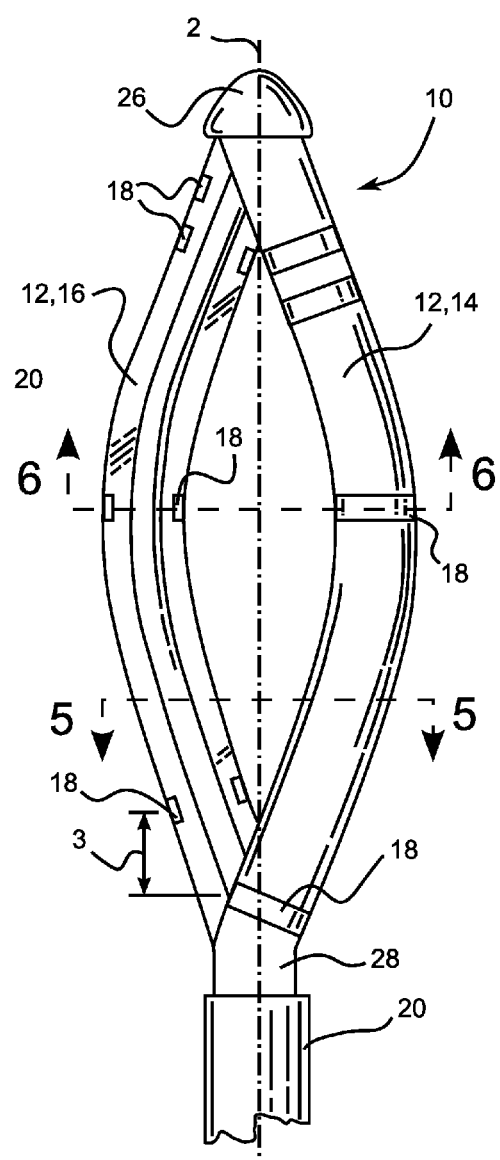
FIG. 4 is an elevation view of the medical stimulation lead of FIG. 1 shown in an expanded position.
Figure 3:
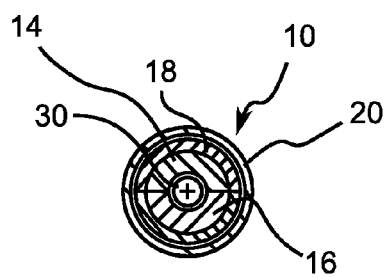
FIG. 3 is a cross-section view of the medical stimulation lead of FIG. 1 taken along line 3-3 of FIG. 1.
Figure 6:
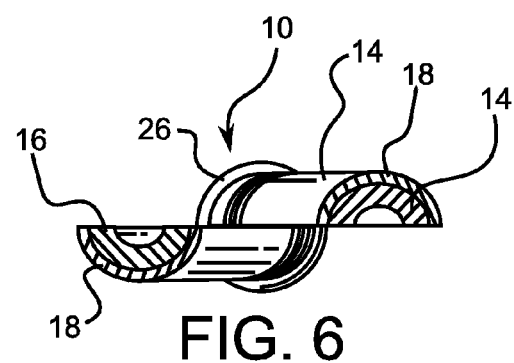
FIG. 6 is a cross-section view of the medical stimulation lead of FIG. 4 taken along line 6-6 of FIG. 4.
Figure 2:
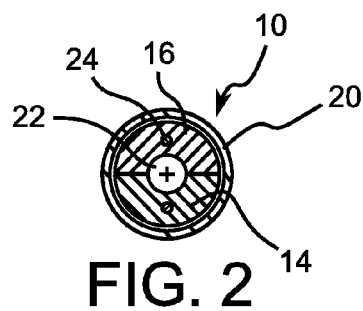
FIG. 2 is a cross-section view of the medical stimulation lead of FIG. 1 taken along line 2-2 of FIG. 1.
Figure 5:
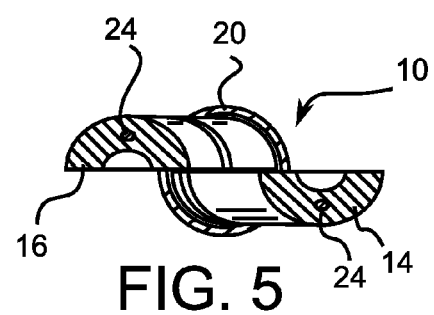
FIG. 5 is a cross-section view of the medical stimulation lead of FIG. 4 taken along line 5-5 of FIG. 4.

Referring to FIGS. 1-10, a medical stimulation lead 10 according to a first preferred embodiment of the present invention is shown. FIGS. 1-3 and 9 show the medical stimulation lead 10 in a contracted position. FIGS. 4-8 and 10 show the medical stimulation lead 10 in an expanded position. The medical stimulation lead 10 includes an elongated lead body 12 having a substantially rounded cross-section. The elongated lead body 12 includes a first biased portion 14 forming a first section of the substantially rounded cross-section and a second biased portion 16 forming a second section of the substantially rounded cross-section. Electrodes 18 are connected to the first and second biased portions 14, 16 of the elongated lead body 12 for conducting current. A restraining body in the form of an outer cannula 20 is removably connected to the elongated lead body 12 releasably exerting a force substantially counter to the biases of the first biased portion 14 and the second biased portion 16, releasably maintaining the substantially rounded cross-section of the elongated lead body 12, wherein a sliding removal of the outer cannula 20 permits the biased portions 14, 16 to expand, dividing the substantially rounded cross-section of the elongated lead body 12. FIGS. 2 and 3 show the cross-section of the elongated lead body 12 as undivided, corresponding to the contracted position. FIGS. 5 and 6 show the cross-section of the elongated lead body 12 as divided, corresponding to the expanded position.

Preferably, as shown in FIGS. 1-10, the elongated lead body 12 has a substantially elliptical cross-section and a longitudinal axis, wherein removal of the outer cannula 20 permits the first biased portion 14 and the second biased portion 16 to expand away from the longitudinal axis 2, dividing the substantially elliptical cross-section. More preferably, as shown in the FIGS. 1-10, the elliptical cross-section is a substantially circular cross-section centered on the longitudinal axis 2, the biased portions 14, 16 contact each other along a plane, and the biased portions 14, 16 are configured to expand away from the longitudinal axis in approximately opposite directions while maintaining slideable contact with each other along the plane. The first biased portion 14 forms a substantially semi-circular section of the substantially circular cross-section, and the second biased portion 16 forms another substantially semi-circular section of the substantially circular cross-section. The semi-circular sections are arced forming a through aperture 22 running along the longitudinal axis 2.

At a first end of the biased portions 14, 16, the biased portions 14, 16 are connected together via a nose cone 26. At a second end of the biased portions 14, 16, the biased portions 14, 16 are joined together at a transition area 28 of the elongated lead body 12. Preferably, the biased portions 14, 16 are constructed by providing a slit of a predetermined length through a flexible tube comprising the elongated lead body 12 along the longitudinal axis 2 of the elongated lead body 12. Thereafter, the resulting biased portions 14, 16 may be biased through suitable treatment process which may include the application of one or more of force, pressure, heat, and stress inducing chemicals. Alternatively, the biased portions 14, 16 may be preformed and thereafter attached in a suitable manner at their ends to a flexible tube to form the complete elongated lead body 12.

During the process of expanding, the biased portions 14, 16 bow outwardly from the longitudinal axis 2 forming opposing bows such that a greatest width of expansion occurs approximately mid-distance between the nose cone 26 and the transition area 28. Configured as described herein, the biased portions 14, 16, once bowed as shown in FIGS. 4 and 10, may be easily straightened, forming the substantially circular cross-section shown in FIGS. 2 and 3, by simply advancing the outer cannula 20 toward the bowed biased portions 14, 16, thereby returning the elongated lead body 12 to a contracted position as shown in FIGS. 1 and 9.

The elongated lead body 12 preferably includes a circumferential protrusion 42 which provides a resisting force to prevent the outer cannula 20 from inadvertently sliding away from a fully advanced position against the nose cone 26, as shown in FIG. 9. When a predetermined amount of force is manually applied to the outer cannula 20, the outer cannula 20 is withdrawn over the circumferential protrusion 42 causing a slight bulge in the outer cannula 20 in the area of the circumferential protrusion 42, as shown in FIG. 10. The circumferential protrusion 42 may also assist a user in determining when the outer cannula 20 is fully advanced against the nose cone 26 of the elongated lead body 12. Alternatively, any suitable resistance feature may be provided, such as grooves and detents, for providing a resisting force releasably maintaining the outer cannula 20 in a position over the biased portions 14, 16.

The electrodes 18 are preferably formed of a conductive metallic material. Each of the electrodes 18 include an arced surface positioned substantially flush with a surface of the biased portion 14, 16 on which it is attached. Accordingly, sharp edges are minimized avoiding injury to a patient using the medical stimulation lead 10. Conducting wires 24 are integrally positioned within the first and second biased portions 14, 16 and electrically connected to the electrodes 18 for providing current through the electrodes. Preferably, the electrodes 18 on first biased portion 14 are not electrically connected to the electrodes 18 on the second biased portion 14. Accordingly, during use of the medical stimulation lead 10, electric potential is provided to the electrodes 18 through the conducting wires 24, and current is conducted from the electrodes 18 on the first biased portion 14 to the electrodes 18 on the second biased portion 16 through a portion of a body of a patient in which the medical stimulation lead 10 is installed. Alternatively, different electrodes 18 on a same one of the biased portions 14, 16 may be connected with separate non-electrically connected conducting wires 24, wherein during use of the medical stimulation lead 10, electrodes on a same one of the biased portions 14, 16 may be provided with differing electric potential, whereby current may be conducted through the body of a patient between separate electrodes 18 connected to a same one of the biased portions 14, 16. The conducting wires 24 are preferably connected to contact elements 25 at an end of the elongated lead body 12. The contact elements 25 are configured for connection to a suitable source of electric potential which preferably includes a programmable pulse generator connected to a battery or other suitable power source. Such pulse generator preferably selectively provides polarities, currents, electric potentials and electric frequencies to the contact elements 25 as required for a particular treatment, and such pulse generator preferably includes a feedback sensor and processor for automatic adjustment of one or more of the polarities, currents, electric potentials and electric frequencies.

A plurality of the electrodes 18 on the first biased portion 14 are preferably offset along the length of the elongated lead body 12, as defined by the longitudinal axis 2, a predetermined distance 3 from respective corresponding electrodes 18 on the second biased portion 16. Such offset between electrode pairs is instrumental in assisting a medical professional in orienting and determining the orientation of the elongated lead body 12 within the body of a patient under a fluoroscope or other device suitable for detecting metallic materials.

The elongated lead body 12, including the first biased portion 14 and the second biased portion 16, is preferably formed from a suitable elastic polymeric material. The elastic polymeric material is preferably insulating and non-conducting such that during use current may flow through the electrodes 18 and conducting wires 24 without flowing through the elongated lead body 12. The outer cannula 20 is also preferably formed from a suitable elastic polymeric material.

The nose cone 26 includes a blind aperture 30 which is configured to connect with a stylus 32, which may be used in directing the medical stimulation lead 10 into a desired position within a patient. The stylus 32 is preferably inserted through the through aperture 22 of the elongated lead body 12 into the blind aperture 30 of the nose cone 26. The stylus is removably retained within the blind aperture 30 by frictional force, or alternatively via any suitable retaining configuration.

Figure 7:
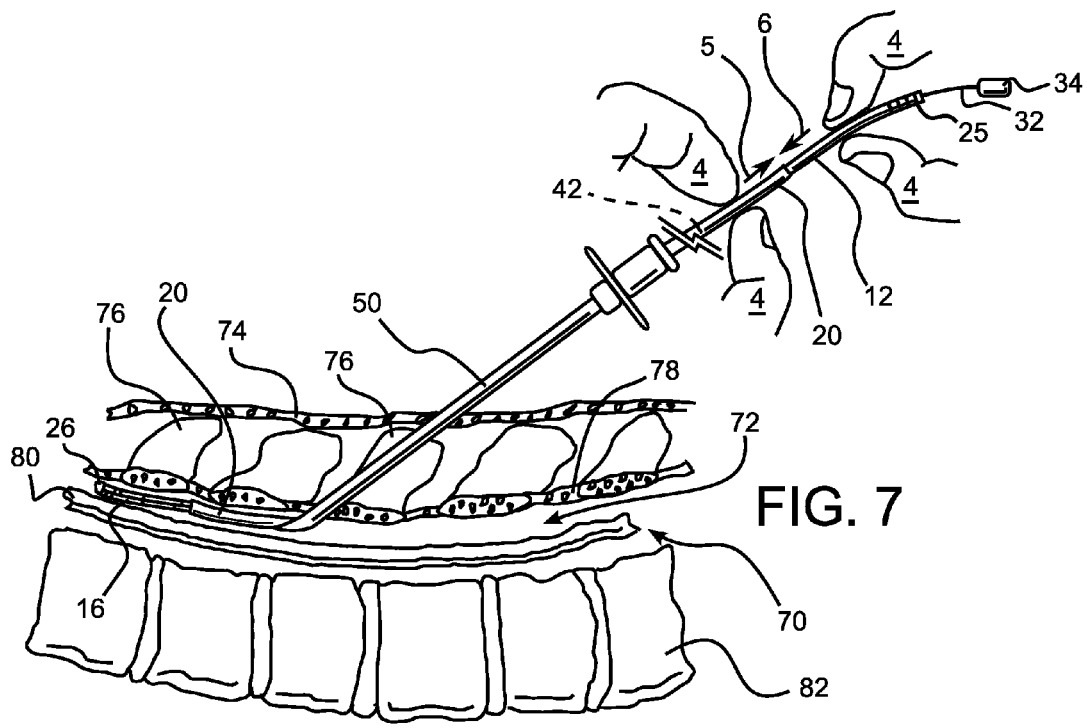
FIG. 7 is a side elevation cross-section view showing insertion of the medical stimulation lead of FIG. 1 into the spinal canal of a patient.
Figure 8:
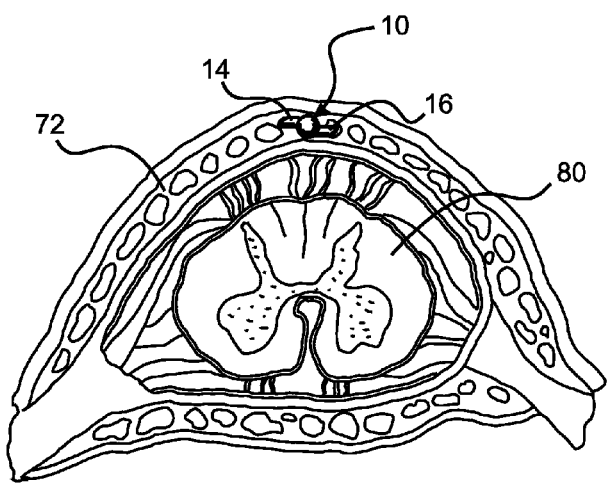
FIG. 8 is a front elevation cross-section view showing insertion of the medical stimulation lead of FIG. 1 into the spinal canal of a patient.

Referring to FIGS. 7 and 8, the medical stimulation lead 10 is shown during a placement procedure in which the medical stimulation lead 10 is inserted into the posterior epidural space 72 in the spinal canal 70 of a patient. During the placement procedure, the medical stimulation lead 10 is preferably loaded into an epidural needle 50 with the stylus 32 connected through the elongated lead body 12 to the nose cone 26 as described above. The end of the epidural needle 50 is inserted through the patient's skin 74 and past the spinous process 76 through the ligamentum flavum 78 into the epidural space 72, and the medical stimulation lead 10 is dispatched through the end of the epidural needle 50 into the epidural space 72 adjacent to the spinal cord 80 opposite the vertebral body 82.

A handle 34 is connected to the stylus 32 facilitating the process of translating and rotating the medical stimulation lead 10, including the elongated lead body 12 and the outer cannula 20, to position the medical stimulation lead 10 in a desired position within the epidural space 72. When the medical stimulation lead 10 is positioned as desired, the stylus 32 is removed by pulling the stylus 32 preferably via the stylus handle 34 away from the insertion location of the epidural needle 50. During positioning of the medical stimulation lead 10 or after the medical stimulation lead 10 is positioned as desired, the outer cannula 20 is manually retracted a predetermined distance away from the nose cone 26, but preferably not completely withdrawn from the epidural space 72, to permit the biased portions 14, 16 of the elongated lead body 12 to bow outwardly away from the longitudinal axis 2. Retraction of outer cannula 20 is preferably accomplished by manually, with a user's fingers 4, by pulling the outer cannula 20 in the direction shown by the arrow 5 relative to the elongated lead body 12 and/or by pushing the elongated lead body 12 in the direction shown by the arrow 6 relative to the outer cannula 20. The epidural needle 50 is removed after positioning of the medical stimulation lead 10. The medical stimulation lead 10, including the outer cannula 20 and the elongated lead body 12, is preferably attached to the skin 74 via stitches or adhesive, and the conducting wires 24 are connected to a suitable source of electric potential via the contact elements 25. When the medical stimulation lead 10 requires repositioning or removal, the outer cannula 20 is preferably advanced by pushing the outer cannula 20 in a direction opposite to the direction shown by the arrow 5 relative to the elongated lead body 12 and/or by pulling the elongated lead body 12 in a direction opposite to the direction shown by the arrow 6 relative to the outer cannula 20, thereby straightening the bowed biased portions 14, 16 and re-forming the substantially rounded cross-section of the elongated lead body 12 facilitating repositioning and removal.

While not wishing to be bound by any theory of functionality of the above-described medical stimulation lead 10, the circular cross-section of the elongated lead body 12 provides the benefit of preventing irritation during positioning of the elongated lead body 12 within the epidural space 72. As configured, the outer cannula 20 is withdrawn at least half a length of the biased portions 114, 116 prior to significant expansion of the biased portions 114, 116. Accordingly, even when the outer cannula 20 is retracted a distance of half the length of the biased portions 114, 116, rotation of the elongated lead body 12 is possible. Rotation of the elongated lead body 12 is important for proper positioning. Therefore the rounded shape the elongated lead body 12, devoid of edges and sharp transitions, facilitates positioning of the elongated lead body 12. While a circular cross-section is most preferred for the cross-section of the elongated lead body 12 in a contracted state, alternatively, other rounded cross-sections may also be acceptable including polygons with sufficiently rounded edges, irregular shapes with sufficiently rounded edges and non-circular ellipses.

Figure 15:
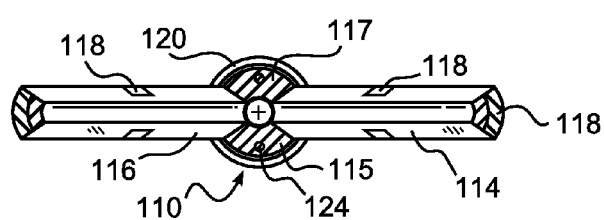
FIG. 15 is a cross-section view of the medical stimulation lead of FIG. 11 taken along line 15-15 of FIG. 11.
Figure 16:
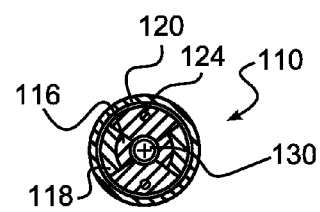
FIG. 16 is a cross-section view of the medical stimulation lead of FIG. 12 taken along line 16-16 of FIG. 12.
Figure 13:
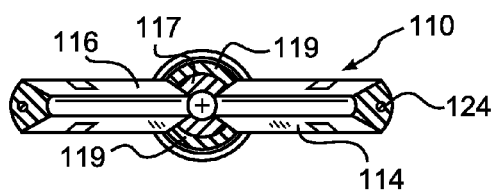
FIG. 13 is a cross-section view of the medical stimulation lead of FIG. 11 taken along line 13-13 of FIG. 11.
Figure 14:
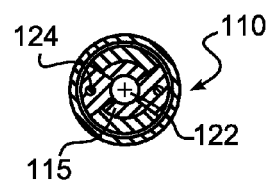
FIG. 14 is a cross-section view of the medical stimulation lead of FIG. 12 taken along line 14-14 of FIG. 12.

Referring to FIGS. 11-16, a medical stimulation lead 110 according to a second preferred embodiment of the present invention is shown. FIGS. 12, 14, and 16 show the medical stimulation lead 110 in a contracted position. FIGS. 11, 13, and 15 show the medical stimulation lead 110 in an expanded position. The medical stimulation lead 110 includes an elongated lead body 112 having a substantially rounded cross-section, which is preferably, as shown, a substantially circular cross-section centered on a longitudinal axis 102. The elongated lead body 112 includes a first biased portion 114 forming a first section of the substantially rounded cross-section and a second biased portion 116 forming a second section of the substantially rounded cross-section. The elongated lead body 112 further includes a first substantially unbiased elongated portion 115, forming a third section of the substantially rounded cross-section, and a second substantially unbiased elongated portion 117, forming a fourth section of the substantially rounded cross-section. Electrodes 118 are connected to the first and second biased portions 114, 116, and other electrodes 119 are connected to the first and second unbiased portions 115, 117.

A restraining body in the form of an outer cannula 120 is removably connected to the elongated lead body 112 releasably exerting a force substantially counter to the biases of the first biased portion 114 and the second biased portion 116, releasably maintaining the substantially rounded cross-section of the elongated lead body 112. A sliding removal of the outer cannula 20 permits the biased portions 114, 116 to expand, dividing the substantially rounded cross-section of the elongated lead body 112, the unbiased portions 115, 117 remaining unexpanded. FIGS. 14 and 16 show the cross-section of the elongated lead body 112 as undivided, corresponding to the contracted position. FIGS. 13 and 15 show the cross-section of the elongated lead body 112 as divided, corresponding to the expanded position. Conducting wires 124 are integrally positioned within the first and second biased portions 114, 116 and the first and second unbiased portions 115, 117. The conducting wires 124 are electrically connected to the electrodes 118, 119 for providing current through the electrodes 118, 119. The biased and unbiased portions 114, 115, 116, 117 are connected via a nose cone 126 which includes a blind aperture 130 configured to connect with a stylus 32, of the type described above with respect to the first preferred embodiment of the present invention, which may travel through a through aperture 122 in the elongated lead body 112 running along the longitudinal axis 102.

Each electrode 118 connected to the first biased portion 114 is preferably aligned with an electrode 118 connected to the second biased portion 116 along a line running perpendicular to the longitudinal axis 102, thereby forming an aligned pair of the electrodes 118. Each electrode 119 connected to the first unbiased portion 115 is preferably aligned with an electrode 119 connected to the second unbiased portion 117 along another line running perpendicular to the longitudinal axis 102, thereby forming an aligned pair of the electrodes 119. Each aligned pair of the electrodes 118 of the biased portions 114, 116 is offset along the length of the elongated lead body 112, as defined by the longitudinal axis 102, a predetermined distance 103 from a respective corresponding aligned pair of the electrodes 119 of the unbiased portions 115, 117. Such offset between electrode pairs is instrumental in assisting a medical professional in orienting and determining the orientation of the elongated lead body 112 within the body of a patient under a fluoroscope or other device suitable for detecting metallic materials.

Figure 17:
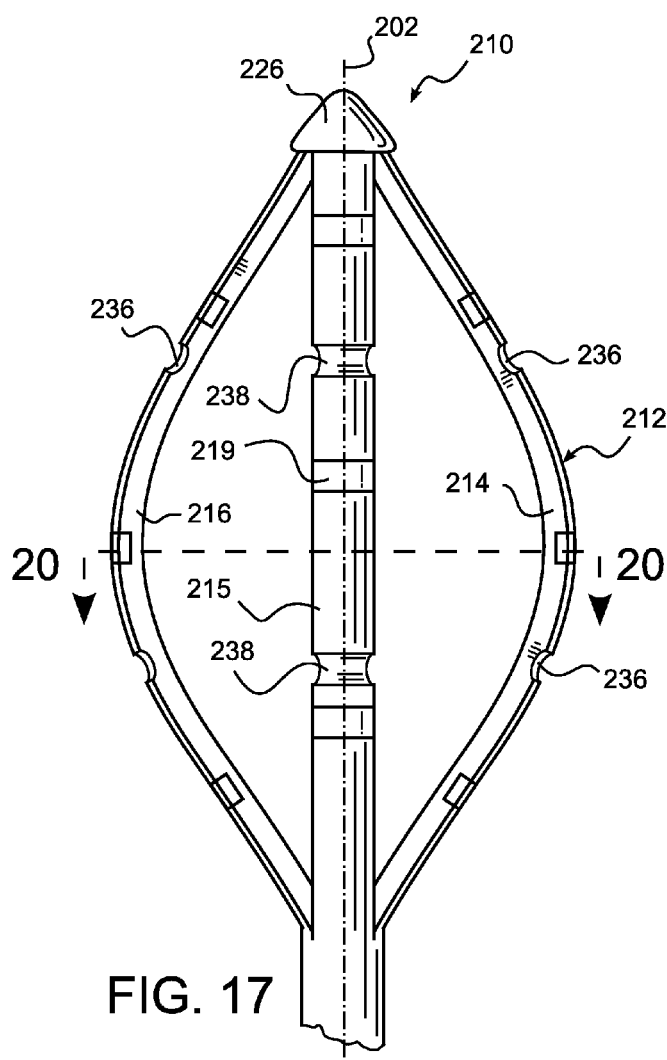
FIG. 17 is a front elevation view of a medical stimulation lead in an expanded position according to a third preferred embodiment of the present invention.
Figure 18:
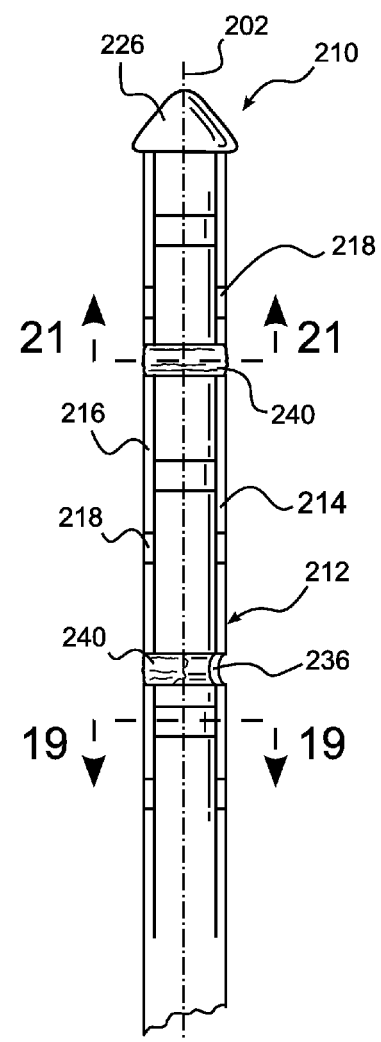
FIG. 18 is a front elevation view of the medical stimulation lead of FIG. 17 shown in a contracted position.

Referring to FIGS. 17-21, a medical stimulation lead 210 according to a third preferred embodiment of the present invention is shown. FIGS. 18, 19, and 21 show the medical stimulation lead 210 in a contracted position. FIGS. 17 and 20 show the medical stimulation lead 210 in an expanded position. The medical stimulation lead 210 includes an elongated lead body 212 having a substantially rounded cross-section, which is preferably a substantially circular cross-section centered on a longitudinal axis 202, as shown. The elongated lead body 212 includes a first biased portion 214 forming a first section of the substantially rounded cross-section and a second biased portion 216 forming a second section of the substantially rounded cross-section. The elongated lead body 212 further includes a first substantially unbiased elongated portion 215, forming a third section of the substantially rounded cross-section, and a second substantially unbiased elongated portion 217 forming a fourth section of the substantially rounded cross-section. Electrodes 218 are connected to the first and second biased portions 214, 216, and other electrodes 219 are connected to the first and second unbiased portions 215, 217. The first and second biased portions 214, 216 include grooves 236, and the first and second unbiased portions 215, 217 include grooves 238 aligned with the grooves 236 in a contracted position of the biased portions 214, 216 along a line perpendicular to the longitudinal axis 202.

Restraining bodies in the form of a plurality of dissolvable sutures 240 are dissovably wrapped around the elongated lead body 212 within the grooves 236, 238 exerting a force substantially counter to the biases of the first biased portion 214 and the second biased portion 216, releasably maintaining the substantially rounded cross-section of the elongated lead body 212. The dissolvable sutures 240 are preferably of a suitable type which dissolve in the presence of biological fluids and are absorbable within the body of a patient in which the medical stimulation lead 210 is inserted. Resting within the grooves 236, 238, the dissolvable sutures 240 do not protrude a significant distance from the surface of the elongated lead body 212, reducing the risk of injury or irritation to a patient, especially during insertion and positioning of the medical stimulation lead 210. Within a period of time after the medical stimulation lead 210 is inserted into a patient's body, the dissolvable sutures 240 dissolve and fracture permitting the first biased portion 214 and the second biased portion 216 to expand away from the longitudinal axis 202, dividing the substantially rounded cross-section of the elongated lead body 212, the unbiased portions 215, 217 remaining unexpanded.

FIGS. 18 and 19 show the cross-section of the elongated lead body 212 as undivided, corresponding to the contracted position. FIG. 20 shows the cross-section of the elongated lead body 212 as divided, corresponding to the expanded position.

Conducting wires 224 are integrally positioned within the first and second biased portions 214, 216 and the first and second unbiased portions 215, 217. The conducting wires 224 are electrically connected to the electrodes 218, 219 for providing current through the electrodes 218, 219. The biased and unbiased portions 214, 215, 216, 217 are connected via a nose cone 226 which includes a blind aperture 230 configured to connect with a stylus 32, of the type described above with respect to the first preferred embodiment of the present invention, which may travel through a through aperture 222 in the elongated lead body 212 running along the longitudinal axis 202.

Figure 22:
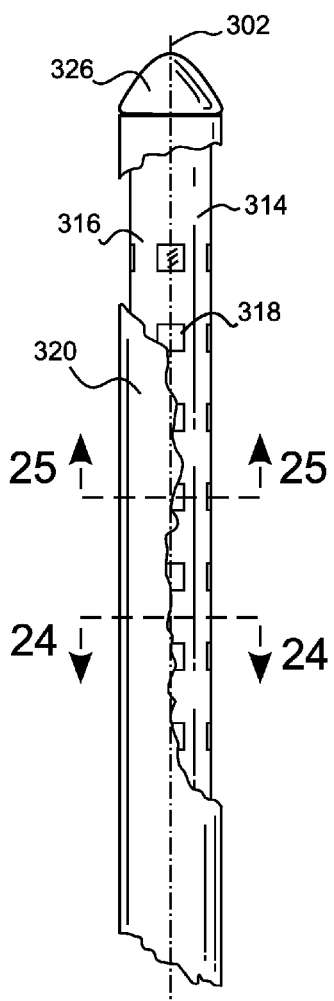
FIG. 22 is a front elevation view of a medical stimulation lead in a contracted position according to a fourth preferred embodiment of the present invention.
Figure 23:
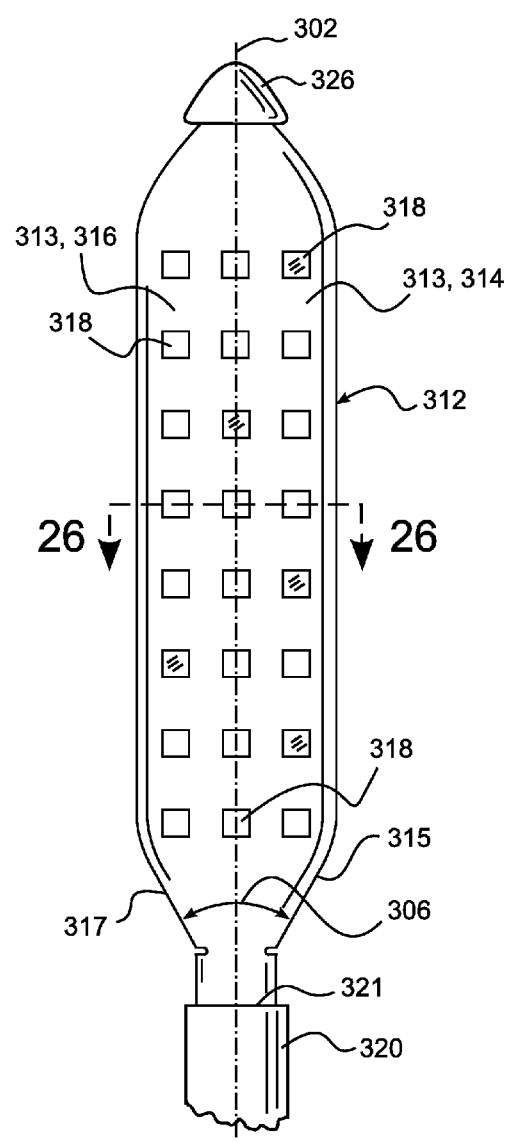
FIG. 23 is a front elevation view of the medical stimulation lead of FIG. 22 shown in an expanded position.
Figure 25:
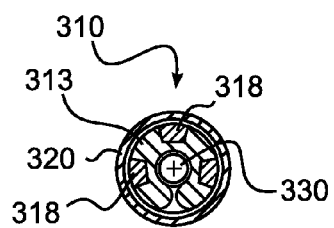
FIG. 25 is a cross-section view of the medical stimulation lead of FIG. 22 taken along line 25-25 of FIG. 22.
Figure 26:
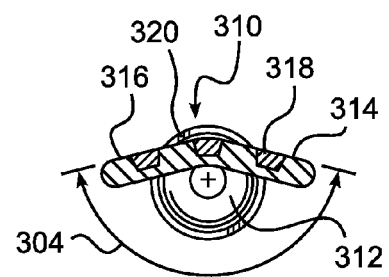
FIG. 26 is a cross-section view of the medical stimulation lead of FIG. 23 taken along line 26-26 of FIG. 23.
Figure 24:
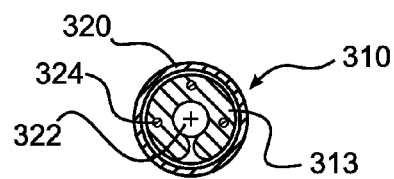
FIG. 24 is a cross-section view of the medical stimulation lead of FIG. 22 taken along line 24-24 of FIG. 22.

Referring to FIGS. 22-26, a medical stimulation lead 310 according to a fourth preferred embodiment of the present invention is shown. FIGS. 22, 24, and 25 show the medical stimulation lead 310 in a contracted position. FIGS. 23 and 26 show the medical stimulation lead 310 in an expanded position. The medical stimulation lead 310 includes an elongated lead body 312 comprising an elastically deformable elongated plate 313. The elongated plate 313 includes a first surface 314 and a second surface 316 which in an undeformed state, as shown in FIGS. 23 and 26, forms a first angle 304 with respect to the first surface 314 along an axis 302 running longitudinally along the length of the elongated plate 312. The first surface 314 includes a first edge 315, and the second surface 316 includes a second edge 317, wherein the first edge 315 forms an acute angle 306 with the second edge 317. The elongated plate 313 is releasably rollable into a substantially cylindrical form, as shown in FIGS. 22, 24 and 25. Electrodes 318 are connected to the elongated plate 313 for conducting current.

A restraining body in the form of an outer cannula 320 is slideably and removably connected to the elongated lead body 312 removably surrounding the elongated plate 313 releasably exerting a force on the elongated plate 313 to releasably maintain the substantially cylindrical form of the elongated plate 313. An end 321 of the outer cannula 320 is in removable and slideable contact with the first edge 315 of the first surface 314 and the second edge 317 of the second surface 316 of the elongated plate 313. Configured in the manner as described, the outer cannula 320 is able to elastically deform the elongated plate 320 into the substantially cylindrical form by moving the outer cannula 320 toward the elongated plate 313 and contacting the end 321 of the outer cannula 320 with the first and second edges 315, 317 of the elongated plate 313 and sliding the outer cannula 320 over the elongated plate 313.

Conducting wires 324 are integrally positioned within the first and second biased portions 314, 316 and the first and second unbiased portions 315, 317. The conducting wires 324 are electrically connected to the electrodes 318 for providing current through the electrodes 318. The elongated plate 313 is connected to a nose cone 326 which includes a blind aperture 330 configured to connect with a stylus 32, of the type described above with respect to the first preferred embodiment of the present invention, which may travel through a through aperture 322 in the elongated lead body 312.

Figure 27:
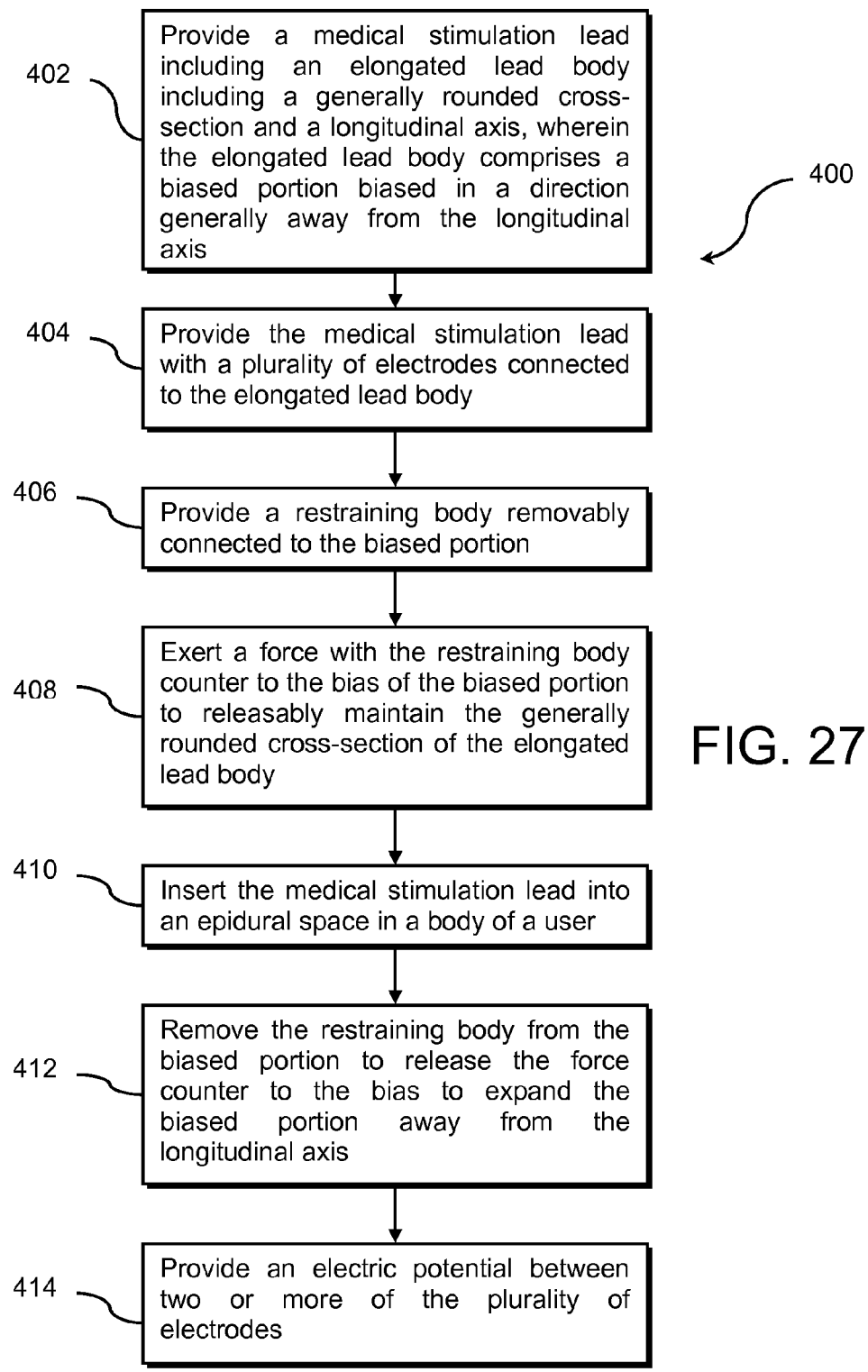
FIG. 27 is a flow chart showing a method for providing spinal cord stimulation according to a preferred embodiment of the present invention.

Referring to FIG. 27, a diagram showing a method 400 for providing spinal cord stimulation according to a preferred embodiment of the present invention is provided. The method 400 includes providing a medical stimulation lead including an elongated lead body including a substantially rounded cross-section and a longitudinal axis, wherein the elongated lead body includes a biased portion biased in a direction substantially away from the longitudinal axis (step 402). The method further includes providing the medical stimulation lead with a plurality of electrodes connected to the elongated lead body (step 404), and providing a restraining body removably connected to the biased portion (step 406). A force counter to the bias of the biased portion is exerted with the restraining body to maintain the substantially rounded cross-section of the elongated lead body (step 408). The medical stimulation lead is inserted into an epidural space in a body of a user (step 410). The restraining body is removed from the biased portion to release the force counter to the bias to expand the biased portion away from the longitudinal axis, dividing the substantially rounded cross-section and stabilizing the medical stimulation lead in the epidural space (step 412). An electric potential between two or more of the plurality of electrodes is provided (step 414).

While the preferred embodiments of the invention have been described in detail above, the invention is not limited to the specific embodiments described above, which should be considered as merely exemplary. Further modifications and extensions of the present invention may be developed, and all such modifications are deemed to be within the scope of the present invention as defined by the appended claims.

What is claimed is:

1. A medical stimulation lead comprising:
an elongated lead body biased in directions substantially limited to one plane, the elongated lead body comprising a substantially rounded cross-section formed by a first biased portion and a second biased portion in an unexpanded configuration, wherein in the unexpanded configuration the first biased portion forms a first section of the substantially rounded cross-section and the second biased portion forms a second section of the substantially rounded cross section, and wherein the first biased portion is biased in a first direction substantially within the one plane, and the second biased portion is biased in a second direction substantially within the one plane and substantially opposite the first direction;
a plurality of electrodes connected to the elongated lead body for conducting current; and
a restraining body removably connected to the elongated lead body releasably exerting a force substantially counter to the biases of the first biased portion and the second biased portion, releasably maintaining the substantially rounded cross-section of the elongated lead body in the unexpanded configuration, wherein removal of the restraining body permits the first biased portion and the second biased portion of the elongated lead body to expand into an expanded configuration, dividing the substantially rounded cross-section;
wherein the first biased portion and the second biased portion of the medical stimulation lead are configured to stabilize the medical stimulation lead in an epidural space adjacent to a spinal cord when the first and second biased portions are in the expanded configuration.

2. The medical stimulation lead of claim 1, wherein the elongated lead body comprises a substantially elliptical cross-section and a longitudinal axis, wherein removal of the restraining body permits the first biased portion and the second biased portion to expand away from the longitudinal axis, dividing the substantially elliptical cross-section.

3. The medical stimulation lead of claim 2, wherein the elongated lead body comprises a substantially circular cross-section and a longitudinal axis, wherein removal of the restraining body permits the first biased portion and the second biased portion to expand away from the longitudinal axis in approximately opposite directions, dividing the substantially circular cross-section.

4. The medical stimulation lead of claim 1, wherein the first section comprises a first arced section of the substantially rounded cross-section of the elongated lead body, and the second section comprises a second arced section of the substantially rounded cross-section of the elongated lead body.

5. The medical stimulation lead of claim 4, wherein each of the plurality of electrodes comprises an arced surface positioned substantially flush with a surface of at least one of the first biased portion and the second biased portion.

6. The medical stimulation lead of claim 1, wherein the first biased portion contacts the second biased portion along the one plane, wherein the first biased portion comprises approximately one half of the substantially rounded cross-section of the elongated lead body, wherein the second biased portion comprises approximately one half of the substantially rounded cross-section of the elongated lead body, and wherein the first biased portion and the second biased portion are in slideable contact along the one plane.

7. The medical stimulation lead of claim 6, wherein the elongated lead body comprises a substantially circular cross-section, wherein the first biased portion forms a substantially semi-circular section of the substantially circular cross-section, and wherein the second biased portion forms another substantially semi-circular section of the substantially circular cross-section.

8. The medical stimulation lead of claim 1, wherein the elongated lead body is further formed by a first substantially unbiased elongated portion forming a third section of the substantially rounded cross-section.

9. The medical stimulation lead of claim 8, wherein a first one of the plurality of electrodes is connected to the first biased portion, a second one of the plurality of electrodes is connected to the second biased portion, and a third one of the plurality of electrodes is connected to the first substantially unbiased elongated portion, and wherein at least one of the first one of the plurality of electrodes and the second one of the plurality of electrodes is offset a predetermined distance from the third one of the plurality of electrodes along a length of the elongated lead body.

10. The medical stimulation lead of claim 8, wherein the elongated lead body is further formed by a second substantially unbiased elongated portion forming a fourth section of the substantially rounded cross-section.

11. The medical stimulation lead of claim 1, wherein the second biased portion is biased in a direction substantially away from the first biased portion, wherein a first one of the plurality of electrodes is connected to the first biased portion and a second one of the plurality of electrodes is connected to the second biased portion offset a predetermined distance from the first one of the plurality of electrodes along a length of the elongated lead body.

12. The medical stimulation lead of claim 1, wherein the second biased portion is biased in a direction substantially away from the first biased portion, wherein the plurality of electrodes comprise a plurality of electrode pairs, wherein each of the plurality of electrode pairs comprises a first electrode connected to the first biased portion and a second electrode connected to the second biased portion offset a predetermined distance from the first electrode along a length of the elongated lead body.

13. The medical stimulation lead of claim 1, wherein the elongated lead body comprises a longitudinal axis, wherein the first biased portion and the second biased portion are biased in a direction away from the longitudinal axis, wherein the restraining body comprises an outer cannula slideably positioned around the elongated lead body, wherein sliding the outer cannula away from the first biased portion and the second biased portion along the longitudinal axis permits the first biased portion and the second biased portion to expand away from the longitudinal axis, dividing the substantially rounded cross-section.

14. The medical stimulation lead of claim 13, wherein the elongated lead body comprises at least one resistance feature providing a resisting force releasably maintaining the outer cannula in a position over the first biased portion and the second biased portion, wherein a predetermined amount of force is required to slide the outer cannula away from the first biased portion and the second biased portion along the longitudinal axis in opposition to the resisting force of the resistance feature.

15. The medical stimulation lead of claim 1, wherein the restraining body comprises at least one dissolvable suture around the elongated lead body in contact with the first biased portion and the second biased portion, and wherein the at least one dissolvable suture is dissolvable in the presence of biological fluids to permit the first biased portion and the second biased portion to expand, dividing the substantially rounded cross-section.

16. The medical stimulation lead of claim 1, further comprising a nose cone connected to the elongated lead body having a substantially rounded shape and a blind aperture, wherein the elongated lead body comprises a through aperture running substantially axially therethrough, and wherein the nose cone is configured to removably receive a stylus through the through aperture of the elongated lead body into the blind aperture.

17. The medical stimulation lead of claim 16, further comprising a stylus positioned within the through aperture of the elongated lead body and removably connected to the blind aperture of the nose cone.

18. The medical stimulation lead of claim 1, wherein the first biased portion and the second biased portion are connected at a first connection point and a second connection point distanced from the first connection point along a longitudinal axis of the elongated lead body, and wherein at least one of the first biased portion and the second biased portion is biased to bow outwardly from the longitudinal axis between the first connection point and the second connection point upon removal of the restraining body.

19. The medical stimulation lead of claim 18, wherein the first connection point is located at an end of the elongated lead body.

20. The medical stimulation lead of claim 1, wherein removal of the restraining body permits the first biased portion and the second biased portion to expand to an expanded position, and replacement of the restraining body forces the first biased portion and the second biased portion to contract to a contracted position, wherein in the contracted position the first biased portion contacts the second biased portion to form a substantially smooth and continuous outer surface of the elongated lead body, and wherein in the expanded position the substantially smooth and continuous outer surface is divided.

21. The medical stimulation lead of claim 20, wherein in the contracted position the elongated lead body comprises a substantially circular cross-section and a longitudinal axis, wherein removal of the restraining body permits the first biased portion and the second biased portion to expand away from the longitudinal axis in approximately opposite directions, dividing the substantially circular cross-section.

22. The medical stimulation lead of claim 20, wherein in the contracted position the elongated lead body comprises a substantially radially symmetric cross-section and a longitudinal axis, wherein removal of the restraining body permits the first biased portion and the second biased portion to expand away from the longitudinal axis in approximately opposite directions, dividing the substantially circular cross-section.

\* \* \* \* \*